US012577182B2

(12) United States Patent
Tanaka

(10) Patent No.: US 12,577,182 B2
(45) Date of Patent: Mar. 17, 2026

(54) METHOD FOR PRODUCING PROPYLENE

(71) Applicant: Sumitomo Chemical Company, Limited, Tokyo (JP)

(72) Inventor: Keisuke Tanaka, Ichihara (JP)

(73) Assignee: SUMITOMO CHECMICAL COMPANY, LIMITED, Tokyo (JP)

( * ) Notice: Subject to any disclaimer, the term of this patent is extended or adjusted under 35 U.S.C. 154(b) by 86 days.

(21) Appl. No.: 18/285,398

(22) PCT Filed: Apr. 25, 2022

(86) PCT No.: PCT/JP2022/018666
§ 371 (c)(1),
(2) Date: Oct. 3, 2023

(87) PCT Pub. No.: WO2022/230791
PCT Pub. Date: Nov. 3, 2022

(65) Prior Publication Data

US 2024/0199511 A1 Jun. 20, 2024

(30) Foreign Application Priority Data

Apr. 26, 2021 (JP) ................................ 2021-074191

(51) Int. Cl.
*C07C 5/333* (2006.01)

(52) U.S. Cl.
CPC ........ *C07C 5/3332* (2013.01); *C07C 2521/12* (2013.01)

(58) Field of Classification Search
CPC ..... C07C 5/3332; C07C 2521/12; C07C 1/24; C07C 11/06; Y02P 20/52; C07B 61/00
USPC ........................................................ 585/444
See application file for complete search history.

(56) References Cited

U.S. PATENT DOCUMENTS

2015/0011813 A1 1/2015 Narula et al.
2016/0122257 A1* 5/2016 Ishibashi .................. B01J 21/04 502/263
2022/0106239 A1* 4/2022 Kapelewski .............. C07C 2/12
2023/0357102 A1 11/2023 Qiao et al.

FOREIGN PATENT DOCUMENTS

CN 104549436 A 4/2015
JP 2008-255104 A 10/2008
WO 2014196517 A1 12/2014
WO 2022089570 A1 5/2022

OTHER PUBLICATIONS

International Search Report issued Jun. 21, 2022 in International Application No. PCT/JP2022/018666.
Mourgues et al., "Kinetics of the Catalytic Dehydration of 2-Propanol," Journal of Catalysis, vol. 7. pp. 117-125 (1967) (cited in the specification).
Written Opinion issued Jun. 21, 2022 in International Application No. PCT/JP2022/018666.
Zhi et al., "Dehydration Pathways of 1-Propanol on HZSM-5 in the Presence and Absence of Water," Journal of the American Chemical Society, vol. 137, pp. 15781-15794 (2015).

* cited by examiner

*Primary Examiner* — Prem C Singh
*Assistant Examiner* — Francis C Campanell
(74) *Attorney, Agent, or Firm* — Panitch Schwarze Belisario & Nadel LLP

(57) ABSTRACT

Provided is a method for efficiently producing propylene from propanol containing a large amount of water. A method for producing propylene includes a dehydration reaction step of dehydrating a raw material containing propanol and water using a catalyst containing silica-alumina, the silica-alumina having a $SiO_2$ content of 3 to 80 in terms of a molar ratio with respect to $Al_2O_3$. The catalyst containing the silica-alumina is produced by a method including a step of carrying out calcination at a calcination temperature of not lower than 400° C. and not higher than 950° C.

6 Claims, No Drawings

METHOD FOR PRODUCING PROPYLENE

CROSS-REFERENCE TO RELATED APPLICATIONS

This application is a Section 371 of International Application No. PCT/JP2022/018666, filed Apr. 25, 2022, which was published in the Japanese language on Nov. 3, 2022 under International Publication No. WO 2022/230791 A1, which claims priority under 35 U.S.C. § 119 (b) to Japanese Application No. 2021-074191, filed Apr. 26, 2021, the disclosures of which are incorporated herein by reference in their entireties.

TECHNICAL FIELD

The present invention relates to a method for producing propylene through dehydration of propanol with use of a catalyst.

BACKGROUND ART

Propylene has been used as a raw material for polypropylene, propylene oxide, aromatic hydrocarbons, aromatic alcohols, and the like. As a method for producing propylene, a method of dehydrating isopropanol (IPA) or normal propanol (NPA) is known. For example, Patent Literature 1 discloses a method for producing propylene with use of a silica gel, as an IPA dehydration catalyst, in which 1000 to 10000 mass ppm of aluminum element is supported. In addition, Non-patent Literature 1 discloses that, in producing propylene with use of silica alumina as an IPA dehydration catalyst, the presence of much water in IPA which serves as a raw material decreases the dehydration rate of IPA.

CITATION LIST

Patent Literature

Patent Literature 1

International Publication No. WO 2014/196517

Non-Patent Literature

Non-Patent Literature 1

De Mourgues et al., JOURNAL OF CATALYSIS 7, 117-125 (1967)

SUMMARY OF INVENTION

Technical Problem

Thus, in the above-described conventional propanol dehydration methods, it was not possible to efficiently produce propylene through dehydration reaction in a case where propanol which served as a raw material contained a large amount of water.

The present invention has been attained in view of the above problem, and an object of the present invention is to provide a method for efficiently producing propylene from propanol containing a large amount of water.

Solution to Problem

As a result of conducting diligent studies to solve the above problem, the inventor and others of the present invention found that the use of a catalyst containing silica alumina which contains $Al_2O_3$ and $SiO_2$ in a specific ratio enables propanol containing a large amount of water to be efficiently converted to propylene through dehydration reaction, and completed the present invention.

That is, the present invention includes the following features:

<1>

A method for producing propylene, the method comprising a dehydration reaction step of dehydrating a raw material containing propanol and water with use of a catalyst containing silica-alumina, the silica-alumina having a $SiO_2$ content of 3 to 80 in terms of a molar ratio with respect to $Al_2O_3$, wherein the catalyst containing the silica-alumina is produced by a production method including a step of carrying out calcination at a calcination temperature of not lower than 400° C. and not higher than 950° C.

<2>

The method according to <1>, wherein a mass of the water in the raw material is 0.01 times to 2 times the mass of the propanol in the raw material.

<3>

The method according to <1> or <2>, wherein a catalyst layer containing the catalyst has a temperature of not higher than 450° C. in the dehydration reaction step.

<4>

The method according to any of <1> to <3>, wherein a fluid produced in the dehydration reaction step contains at least one of olefins represented by the following general formula (1) or (2) in an amount of not more than 0.1 in terms of a molar ratio with respect to the amount of propylene in the fluid,

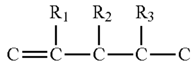

(1)

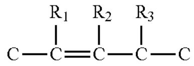

(2)

where, in the general formulas (1) and (2), any one of $R_1$, $R_2$, and $R_3$ is a methyl group, and the others are hydrogen.

Advantageous Effects of Invention

According to an aspect of the present invention, it is possible to provide a method for efficiently producing propylene from propanol containing a large amount of water.

DESCRIPTION OF EMBODIMENTS

1. Method for Producing Propylene

A method for producing propylene in accordance with an embodiment of the present invention includes a dehydration reaction step of dehydrating a raw material containing propanol and water with use of a catalyst containing silica-alumina, the silica-alumina having a $SiO_2$ content of 3 to 80 in terms of a molar ratio with respect to $Al_2O_3$, wherein the catalyst containing the silica-alumina is produced by a production method including a step of carrying out calcination at a calcination temperature of not lower than 400° C. and not higher than 950° C. It can also be said that a molar ratio of $SiO_2$ to $Al_2O_3$ in the silica alumina is 3 to 80.

Hereinafter, a method for producing propylene in accordance with an embodiment of the present invention is also referred to as the present production method. In addition, the catalyst containing the silica alumina is also referred to as a silica-alumina catalyst. The silica-alumina catalyst is used as a dehydration catalyst in the present production method.

With use of the silica-alumina catalyst, it is possible to produce propylene by efficiently dehydrating propanol even in a case where propanol which serves as a raw material contains a large amount of water. In addition, the use of the silica-alumina catalyst achieves dehydration reaction of propanol at a low temperature and thus inhibits the production of a by-product such as olefin having 6 carbon atoms (C6 olefin). This makes it possible to inhibit carbon deposition resulting from the by-product during the production of propylene. Furthermore, the raw material containing water serves as a heating medium for heat of reaction. This makes it possible to make the temperature in a reaction system during the production of propylene more uniform (suppression of temperature distribution), and also improves industrial applicability.

A process by which propylene is produced through dehydration reaction of propanol in the present production method is specifically represented by the following formula (3):

$$C_3H_7OH \rightarrow C_3H_6 + H_2O \quad (3)$$

In the present production method, in a case where isopropanol (IPA) is used as propanol, IPA may be converted to propylene by either intramolecular dehydration or intermolecular dehydration. In a case where intramolecular dehydration of IPA is carried out, propylene is produced directly from IPA. On the other hand, in a case where intermolecular dehydration of IPA is carried out, propylene is produced via diisopropyl ether (DIPE).

Silica-Alumina Catalyst

The silica-alumina catalyst used in the dehydration reaction step of the present production method is produced by a production method including a step of carrying out calcination at a calcination temperature of not lower than 400° C. and not higher than 950° C. In other words, the production method for propylene may include a step of calcining a raw material of a silica-alumina catalyst at a calcination temperature of not lower than 400° C. and not higher than 950° C. to obtain the silica-alumina catalyst. Further, the production method for a silica-alumina catalyst may include an additional production step other than the calcination step.

The silica alumina that is contained in the catalyst used in the dehydration reaction step of the present production method has a $SiO_2$ content of 3 to 80, preferably 4 to 70, more preferably 4 to 60, and even more preferably 4 to 50, in terms of a molar ratio with respect to $Al_2O_3$. The molar ratio can be measured by, for example, an inductively coupled plasma atomic emission spectroscopy method (ICP-AES method) described in Examples which will be described later.

Note that, as will be described later, the catalyst can be used in combination with a molding agent (binder). In a case where silica and/or alumina is/are used as the binder, the molar ratio between $SiO_2$ and $Al_2O_3$ measured by the ICP-AES method is assumed to be a value that includes the amounts of $SiO_2$ and $Al_2O_3$ contained in silica and/or alumina which is/are added as the binder. That is, in a case where the catalyst is used in combination with the binder, the molar ratio between $SiO_2$ and $Al_2O_3$ is measured on the basis of a total value of the catalyst and $SiO_2$ and $Al_2O_3$ which are contained in the binder. The same applies to a case where alumina and/or the like is/are used as a cocatalyst in combination with the silica-alumina catalyst.

In a case where the molar ratio of $SiO_2$ with respect to $Al_2O_3$ in the silica alumina contained in the catalyst is in the above-described range, the proportion of $Al_2O_3$ contained in the catalyst is high as compared to the conventional silica alumina. Thus, a sufficient amount of acid site is secured in the dehydration reaction of propanol. This makes the catalyst highly active even when a large amount of water is contained in propanol which serves as a raw material, and thus makes it possible to efficiently produce propylene.

The silica-alumina catalyst may contain, in addition to $Al_2O_3$ and $SiO_2$, a trace amount of metallic element derived from impurities of the raw material. Examples of such a metallic element include Ca, Fe, Mg, Na, Ti, and Zr. As the silica-alumina catalyst, a commercially available product may be used, or a chemically synthesized product may be used, provided that the molar ratio of $SiO_2$ with respect to $Al_2O_3$ is in the above-described range.

In a case where the silica-alumina catalyst is chemically synthesized, a silicon compound and an aluminum compound can be used as a raw material. Examples of the raw material containing silicon include tetraethyl orthosilicate, silica gel, and sodium silicate. The raw material containing aluminum is preferably water soluble. Specifically, examples of the raw material containing aluminum include aluminum nitrate, aluminum sulfate, and aluminum phosphate. Further, these compounds containing aluminum may be a single substance or may be a hydrate.

A method of synthesizing the silica-alumina catalyst may be, for example, any of the following methods: an impregnation method; and a sol-gel method. As an example, a method of synthesizing the silica-alumina catalyst by a sol-gel method will be presented below. First, a gel is obtained by stirring the above-described raw material containing silicon and the above-described raw material containing aluminum in the presence of a solvent and an organic additive. This reaction is usually carried out by adding a silicon compound to an aqueous solution containing an aluminum compound. Next, the gel thus obtained is dried into powder by air or by an evaporator or the like. After that, the powder thus obtained is calcined, so that it is possible to obtain the silica-alumina catalyst.

As the solvent, water is preferable because water is easy to handle and remove. As the organic additive, citric acid, ethylene glycol, 1,2-propanediol, 1,3-propanediol, 1,4-butanediol, 2,3-butanediol, 2-methyl-2,4-pentanediol, and the like can be used. The calcination temperature for the powder is not lower than 400° C. and not higher than 950° C. A lower limit of the calcination temperature is not lower than 400° C., preferably not lower than 500° C., and more preferably not lower than 600° C. An upper limit of the calcination temperature is not higher than 950° C., preferably not higher than 900° C., and more preferably not higher than 850° C. In another embodiment, the calcination temperature for the powder is not lower than 200° C. or not lower than 300° C. A calcination time is preferably 1 hour to 10 hours and more preferably 2 hours to 9 hours. The calcination of the powder may be carried out a plurality of times. In a case where the calcination is carried out a plurality of times, a heating temperature and a heating time may be identical or may be different. A heating method is not particularly limited. For example, the calcination can be carried out with use of a muffle furnace, a tubular furnace, a rotary kiln, a shaft kiln, or the like.

By carrying out calcination during the production of the silica-alumina catalyst, a chemical bond of Si—O—Al is formed in a resulting silica-alumina catalyst. This allows the resulting silica-alumina catalyst to have an acid site stronger than that of $SiO_2$ alone, $Al_2O_3$ alone, or a mixture of $SiO_2$ and $Al_2O_3$ and have a high activity. Further, the calcination temperature falling within the above-described range allows the resulting silica-alumina catalyst to have higher activity. Thus, the use of such a silica-alumina catalyst for the dehydration of propanol enhances yield of propylene. Further, the calcination temperature being not lower than 400° C. makes it possible to sufficiently remove the organic additive used for the preparation of the silica-alumina catalyst. This allows the silica-alumina catalyst to obtain an adequate acid site and have enhanced moldability. Thus, it is possible to suitably use such a silica-alumina catalyst as the catalyst for the dehydration of propanol.

Raw Material

In the present production method, the raw material to be dehydrated (hereinafter also referred to as the present raw material) contains water and propanol. Propanol includes isopropanol (IPA), normal propanol (NPA), or a mixture in which IPA and NPA are mixed in any proportion.

The mass of water in the present raw material is 0.01 times to 2 times, preferably 0.1 times to 2 times, more preferably 0.5 times to 2 times, and particularly preferably 1.0 times to 2 times, the mass of propanol in the present raw material.

In a case where the content of water in the present raw material is not less than 0.01 times the mass of propanol, deposition of carbons derived from a by-product during the dehydration reaction is inhibited. This brings about the effect of making it possible to produce propylene more efficiently. In addition, since water acts as a heating medium for heat of reaction, it is possible to make the temperature in a reaction system during the production of propylene more uniform (suppression of temperature distribution), and it is possible to efficiently carry out the dehydration reaction. Further, in a case where the content of water in the present raw material is not more than 2 times the mass of propanol in the present raw material, the present raw material sufficiently contains propanol. This leads to an increase in the amount of propylene produced.

The present raw material contains propanol in a proportion of preferably 33% by mass to 99% by mass, more preferably 33% by mass to 90% by mass, and even more preferably 33% by mass to 50% by mass, when the whole present raw material is 100% by mass. In a case where the content of propanol in the present raw material is not more than 99% by mass, the present raw material can contain water. This brings about the above-described effect brought about in the case where the present raw material can contain water. Further, the content of propanol in the present raw material is not less than 33% by mass, the amount of propylene produced increases.

The present raw material may further contain, in addition to water and propanol, an additional component(s), such as impurities, that can be mixed into the present raw material in the process of producing the present raw material. Examples of such an additional component(s) such as impurities include an unreacted raw material used for the production of the present raw material and a by-product produced in the step of producing the present raw material. Examples of such impurities include acetone, methanol, ethylene glycol, dimethyl ether, methyl ethyl ether, and dimethyl carbonate. The content of impurities in the present raw material is not particularly limited, provided that the content of impurities does not affect the production of propylene. The content of impurities in the present raw material is preferably not more than 5% by mass, more preferably not more than 1% by mass, and ideally not contained at all.

Dehydration Reaction Step

The present production method includes a dehydration reaction step of dehydrating the present raw material with use of the above-described silica-alumina catalyst. In the dehydration reaction step, the silica-alumina catalyst may be used after the silica-alumina catalyst has been made into a catalyst layer which is filled into a reactor or the like.

The mode of the reactor used in the dehydration reaction step is not particularly limited, and may be, for example, any of the following modes: a batch mode; a semi-batch mode; and a continuous flow mode. Further, the form in the dehydration reaction step is not particularly limited, and the dehydration reaction step can be carried out in any of the following forms: a liquid phase; a gas phase; and a gas-liquid mixing layer. Furthermore, the filling mode for making the catalyst into the catalyst layer is not particularly limited, and the catalyst layer can be filled in any mode such as a fixed bed, a fluidized bed, a suspended bed, and a staged fixed bed. In addition, in carrying out the dehydration reaction step, a gas component that does not impair the dehydration reaction step may be added. Examples of such a gas component include nitrogen, carbon dioxide, argon, helium, methane, ethane, and propane.

As the catalyst to be made into the catalyst layer, the silica-alumina catalyst alone may be used. Alternatively, the catalyst to be made into the catalyst layer may be used in combination with, for example, a catalyst that can be typically used for dehydration reaction or a molding agent (binder). In a case where the silica-alumina catalyst is used together with a molding agent, the silica-alumina catalyst and the molding agent may be used in the form of a molded body that is obtained by subjecting the silica-alumina catalyst and the molding agent to kneading, extrusion, and molding and that has an increased mechanical strength. Examples of the catalyst that can be typically used for dehydration reaction or the molding agent include silica, alumina, clay, titania, zirconia, zinc oxide, ceria, lanthana, graphite, and ethylcellulose.

The temperature of the catalyst layer during the dehydration reaction step is preferably not higher than 450° C., more preferably not higher than 400° C., even more preferably not higher than 300° C., and particularly preferably not higher than 200° C. A lower limit of the temperature of the catalyst layer is not particularly limited, provided that the lower limit of the temperature of the catalyst layer is not lower than the temperature at which the dehydration reaction step can be carried out. However, the lower limit of the temperature of the catalyst layer can be not lower than 160° C. and can be not lower than 180° C., from the viewpoint of increasing the activity of a resulting catalyst. The temperature of the catalyst layer can be adjusted as appropriate by, for example, a change in temperature of the apparatus for use in dehydration treatment.

The temperature of the catalyst layer being in the above-described range allows the dehydration reaction to be carried out at a relatively low temperature. This makes it possible to reduce energy required for the reaction. Further, oligomerization of propylene and production of a heavy product of propylene are promoted in a high-temperature environment. Thus, carrying out reaction at a temperature lower than heretofore inhibits the production of a by-product and enhances yield of propylene.

The reaction pressure during the dehydration reaction step is not particularly limited, but is preferably 0 KPa to 100000 KPa (gage pressure), more preferably 0 KPa to 5000 KPa (gage pressure), and even more preferably 0 KPa to 4000 KPa (gage pressure).

The ratio (W/F) of the catalyst weight g to the propanol flow rate $mol \cdot h^{-1}$ during the dehydration reaction step is not particularly limited, but is preferably 0.01 $g \cdot h \cdot mol^{-1}$ to 10000 $g \cdot h \cdot mol^{-1}$, more preferably 0.01 $g \cdot h \cdot mol^{-1}$ to 5000 $g \cdot h \cdot mol^{-1}$, and even more preferably 1 $g \cdot h \cdot mol^{-1}$ to 200 $g \cdot h \cdot mol^{-1}$.

In a case where the activity of the catalyst has decreased during the dehydration reaction step, a known method may be used to recover the activity of the catalyst. In addition, in order to maintain the production volume of propylene, a switching method may be employed in which two or more reactors are arranged in parallel, and, while the recovery of the activity of the catalyst is carried out in one reactor, dehydration reaction is carried out in another reactor. Furthermore, in a case where there are three or more reactors, at least two reactors in which the recovery of the activity of the catalyst is not carried out may be connected in series to reduce the fluctuation of the production volume. Further, in a case where the mode of the reactor is a fluidized-bed flow reaction mode or in a moving-bed reaction mode, it is possible to maintain a certain level of catalytic activity by continuously or intermittently extracting the catalyst in whole or in part from the reactor and adding a catalyst in an amount equivalent to the amount of the extracted catalyst. The dehydration reaction step may be followed by, for example, extraction of propylene, which is a product, in a gas-liquid separation step and then followed by a step of carrying out purification by distillation or the like.

2. Product

In the dehydration reaction step of the present production method, dehydration of the present raw material containing propanol is carried out so that a product containing propylene is produced.

The product in the present production method (e.g., a fluid such as a liquid and a gas) can contain impurities, in addition to propylene. Examples of the impurities include water, unreacted propanol, and a by-product. Examples of the by-product include C6 olefin.

The content of the impurities is preferably not more than 0.1, more preferably not more than 0.05, and even more preferably not more than 0.01, in terms of a molar ratio with respect to the content of propylene in the product. Ideally, it is preferable that the impurities are not contained at all in the product.

The fluid produced in the above-described dehydration reaction step of the present production method may contain at least one of olefins represented by the general formula (1) or (2) below. Examples of the olefins represented by the general formula (1) or (2) below include 3-methyl-2-pentene and 2-methyl-1-pentene. A lower limit of the amount of the at least one of the olefins contained may be not less than 0.00000001 in terms of a molar ratio with respect to the amount of propylene in the fluid, may be not less than 0.0000001 in terms of a molar ratio, and may be not less than 0.000001 in terms of a molar ratio. An upper limit thereof may be not more than 0.1 in terms of a molar ratio with respect to the amount of propylene in the fluid, may be not more than 0.05 in terms of a molar ratio, and may be not more than 0.01 in terms of a molar ratio. The olefin represented by the general formula (1) or (2) below corresponds to olefin that has a carbon number of 5 in a main chain and has a methyl group. Ideally, it is preferable that the olefin is not contained in the fluid at all. However, the lower limit of the amount of the olefin contained may be, for example, greater than 0 in a molar ratio. In a case where the olefin is contained in the fluid, carbon may be deposited on the catalyst. The carbon deposited on the catalyst causes a decrease in acid site of the catalyst, which may result in a decrease in catalytic activity.

(1)

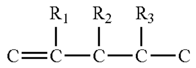

(2)

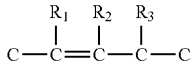

In the formulas (1) and (2), any one of $R_1$, $R_2$, and $R_3$ is a methyl group, and the others are hydrogen.

In the method for producing propylene through propanol dehydration, it is known that an oligomer or the like can be mixed as a by-product. However, the structure of an oligomer is not known, and in particular, C6 olefin with branches within a carbon backbone shown in the formula (1) or (2) above was not known as a by-product. In the production of propylene through propanol dehydration, inhibiting the production of C6 olefin with these branches, which is a by-product, is critical to enhancing propylene yield. This can be said to be an effect that is brought about by the present production method and that could not be expected by a person skilled in the art.

The application for which the propylene obtained by the present production method is used is not particularly limited, but the propylene obtained by the present production method can be suitably used as a raw material for polypropylene, propylene oxide, plastic, aromatic hydrocarbons, aromatic alcohols, and the like.

The present invention is not limited to the embodiments, but can be altered by a skilled person in the art within the scope of the claims. The present invention also encompasses, in its technical scope, any embodiment derived by combining technical means disclosed in differing embodiments.

EXAMPLES

The following will describe Examples of the present invention. However, the present invention is not limited by these Examples.

Measurement Method

In the production of propylene in the Examples, analysis of a liquid component and a gas component exiting a reactor outlet was carried out by gas chromatography, and propylene yield was calculated by the following formula (4):

$$\text{Propylene yield (\%)}=[(\text{propanol supplied [mol/min]}-\text{unreacted propanol [mol/min]})/\text{propanol supplied [mol/min]}]\times[3\times\text{the amount of propylene produced [mol/min]}/(\text{total sum of the amounts of products produced on a carbon basis [mol/min]})]\times 100 \quad (4)$$

Example 1 a. Production Method for Silica-Alumina Catalyst (A)

Put into a 200-ml glass beaker were 60.14 g of pure water, 23.16 g of aluminum nitrate nonahydrate, and 13.05 g of citric acid, and a resulting mixture was stirred at room temperature for 5 minutes. While the stirring of the mixture in the beaker at room temperature was continued, 71.90 g of tetraethyl orthosilicate was dropped over 1 hour from a dropping burette to obtain a gel. The gel was transferred to a porcelain dish, dried in air at room temperature for 24 hours, and then dried in an evaporator under reduced pressure of 160 hPa at a water bath temperature of 50° C. to obtain 95.67 g of powder. After 43.86 g of the powder thus obtained had been calcined in a muffle furnace at 500° C. for 5 hours, the powder was extracted from the muffle furnace to obtain 11.35 g of powder. 10.02 g of the powder thus extracted was placed in the muffle furnace again and was calcined at 600° C. for 2 hours to obtain 10.11 g of silica-alumina catalyst (A). Analysis carried out by the inductively coupled plasma atomic emission spectroscopy method (ICP-AES method) showed that the molar ratio of $SiO_2/Al_2O_3$ in the silica-alumina catalyst (A) was 11.

b. Production of Propylene

The silica-alumina catalyst (A) was pressurized at 60 MPa (gage pressure) for 20 minutes with use of a press machine to obtain a silica-alumina catalyst (A) molded body. Subsequently, the resulting molded body was ground in a meno mortar, was allowed to pass through a sieve of 10 mesh and a sieve of 26 mesh, and was extracted from between the two sieves to obtain powder of the silica-alumina catalyst (A) molded body. 3.08 g of the obtained powder of the silica-alumina catalyst (A) molded body was filled into a SUS reaction tube that had an inner diameter of 1.4 cm and that included a SUS tube which had an outer diameter of 3 mm and which contained a thermocouple, so that a catalyst layer with a filling volume of 5.77 ml was formed. Thereafter, the temperature of the catalyst layer was increased in a reaction tube heating furnace over 45 minutes from room temperature to 200° C. under the flow of nitrogen at a rate of 136.7 N ml/min. A water-containing IPA raw material containing water 1 time as much by mass as IPA was introduced under the flow of nitrogen into a vaporizer heated to 110° C. at a flow rate of 0.298 ml/min with use of a feeding pump, and was then introduced into a reaction tube connected to a rear stage of the vaporizer. After that, the temperature of the reaction tube heating furnace was adjusted so that the temperature of the center of the catalyst layer was about 200° C. After a lapse of 30 minutes since the temperature of the catalyst layer had been adjusted, a liquid from the reaction tube was collected in two glass trap containers containing 26 g of methanol for 36 minutes, and a liquid component was analyzed by gas chromatography. After a lapse of 35 minutes following the collection of the liquid, a gas component exiting from the outlet of the two glass trap containers containing methanol was collected in a gas bag, and the gas component was analyzed by gas chromatography.

Comparative Example 1

(a) Production Method for Silica-Alumina Catalyst (B)

A mixture of 19.31 g of pure water and 0.55 g of aluminum nitrate nonahydrate was prepared in a 100-ml glass beaker, and was dropped, drop by drop, at room temperature into 20 g of CARIACT (Q-30) available from FUJI SILYSIA CHEMICAL LTD. in a 500-ml glass beaker with use of a Pasteur pipette. After the mixture had been dried at 120° C. for 3 hours, 19.85 g of the mixture was placed in a muffle furnace and was calcined at 500° C. for 6 hours to obtain 19.67 g of silica-alumina catalyst (B). Analysis carried out by the ICP-AES method showed that the molar ratio of $SiO_2/Al_2O_3$ in the silica-alumina catalyst (B) was 404. Note that the silica-alumina catalyst (B) corresponds to the catalyst described in Example 4 of Patent Literature 1.

(b) Production of Propylene

Production of propylene was carried out in the same manner as in Example 1 except that 2.12 g of the silica-alumina catalyst (B) was used to form the catalyst layer with a filling volume of 5.77 ml, and analysis of a liquid component and a gas component was carried out in the same manner as in Example 1.

Example 2 a. Production Method for Silica-Alumina Catalyst (C)

Put into a 200-ml glass beaker were 59.73 g of pure water, 5.11 g of aluminum nitrate nonahydrate, and 12.95 g of citric acid, and a resulting mixture was stirred at room temperature for 5 minutes. While the stirring of the mixture in the beaker at room temperature was continued, 71.63 g of tetraethyl orthosilicate was dropped over 1 hour from a dropping burette to obtain a gel. The gel was transferred to a porcelain dish, dried in air at room temperature for 24 hours, and then dried in an evaporator under reduced pressure of 160 hPa at a water bath temperature of 50° C. to obtain 41.55 g of powder. In a muffle furnace, 35.83 g of the powder thus obtained was calcined at 600° C. for 2 hours to obtain 23.10 g of silica-alumina catalyst (C). Analysis carried out by the inductively coupled plasma atomic emission spectroscopy method (ICP-AES method) showed that the molar ratio of $SiO_2/Al_2O_3$ in the silica-alumina catalyst (C) was 51.

b. Production of Propylene

Powder of a silica-alumina catalyst (C) molded body was obtained from the silica-alumina catalyst (C) with use of the press machine and the sieves as in Example 1. Production of propylene was carried out in the same manner as in Example 1 except that the catalyst layer with a filling volume of 5.77 ml was formed after the silica-alumina catalyst (C) molded body had been vacuum-dried at 200° C. for 2 hours and that the temperature of the vaporizer was set to 210° C., and analysis of a liquid component and a gas component was carried out in the same manner as in Example 1.

Example 3 a. Production Method for Silica-Alumina Catalyst (D)

Put into a 200-ml glass beaker were 60.03 g of pure water, 3.67 g of aluminum nitrate nonahydrate, and 13.06 g of citric acid, and a resulting mixture was stirred at room temperature for 5 minutes. While the stirring of the mixture in the beaker at room temperature was continued, 71.54 g of tetraethyl orthosilicate was dropped over 1 hour from a dropping burette to obtain a gel. The gel was transferred to a porcelain dish, dried in air at room temperature for 24 hours, and then dried in an evaporator under reduced pressure of 160 hPa at a water bath temperature of 50° C. to obtain 47.25 g of powder. In a muffle furnace, 46.44 g of the powder thus obtained was calcined at 600° C. for 2 hours to obtain 20.79 g of silica-alumina catalyst (D). Analysis carried out by the inductively coupled plasma atomic emission spectroscopy method (ICP-AES method) showed that the molar ratio of $SiO_2/Al_2O_3$ in the silica-alumina catalyst (C) was 69.

b. Production of Propylene

Powder of a silica-alumina catalyst (D) molded body was obtained from the silica-alumina catalyst (D) with use of the press machine and the sieves as in Example 1. Production of propylene was carried out in the same manner as in Example 1 except that the catalyst layer with a filling volume of 5.77 ml was formed after the silica-alumina catalyst (D) molded body had been vacuum-dried at 200° C. for 2 hours and that the temperature of the vaporizer was set to 210° C., and analysis of a liquid component and a gas component was carried out in the same manner as in Example 1.

Comparative Example 2

Production Method for Silica-Alumina Catalyst (E)

Put into a 200-ml glass beaker were 59.88 g of pure water, 23.17 g of aluminum nitrate nonahydrate, and 13.07 g of citric acid, and a resulting mixture was stirred at room temperature for 5 minutes. While the stirring of the mixture in the beaker at room temperature was continued, 71.67 g of tetraethyl orthosilicate was dropped over 1 hour from a dropping burette to obtain a gel. The gel was transferred to a porcelain dish, dried in air at room temperature for 24 hours, and then dried in an evaporator under reduced pressure of 160 hPa at a water bath temperature of 50° C. to obtain 65.67 g of powder. After 30.40 g of the powder thus obtained had been calcined in a muffle furnace at 300° C. for 2 hours, the powder was extracted from the muffle furnace to obtain 12.47 g of powder of a silica-alumina catalyst (E). This silica-alumina catalyst (E) got a brown coloration because an organic component contained in the prepared raw material had not been removed. In addition, molding was attempted with use of the press machine as in Example 1, but it was not possible to carry out molding.

Example 4 a. Production Method for Silica-Alumina Catalyst (F)

12.30 g of the silica-alumina catalyst (E) was placed in the muffle furnace again and was calcined at 500° C. for 2 hours to obtain 10.11 g of silica-alumina catalyst (F).

b. Production of Propylene

Powder of a silica-alumina catalyst (F) molded body was obtained from the silica-alumina catalyst (F) with use of the press machine and the sieves as in Example 1. Production of propylene was carried out in the same manner as in Example 1 except that the catalyst layer with a filling volume of 5.77 ml was formed after the silica-alumina catalyst (F) molded body had been dried at 200° C. for 2 hours and that the temperature of the vaporizer was set to 210° C., and analysis of a liquid component and a gas component was carried out in the same manner as in Example 1.

Example 5 a. Production Method for Silica-Alumina Catalyst (G)

Put into a 200-ml glass beaker were 60.79 g of pure water, 23.17 g of aluminum nitrate nonahydrate, and 13.02 g of citric acid, and a resulting mixture was stirred at room temperature for 5 minutes. While the stirring of the mixture in the beaker at room temperature was continued, 72.21 g of tetraethyl orthosilicate was dropped over 1 hour from a dropping burette to obtain a gel. The gel was transferred to a porcelain dish, dried in air at room temperature for 24 hours, and then dried in an evaporator under reduced pressure of 160 hPa at a water bath temperature of 50° C. to obtain 62.75 g of powder. In a muffle furnace, 30.52 g of the powder thus obtained was calcined at 900° C. for 1 hour to obtain 11.35 g of silica-alumina catalyst (G).

b. Production of Propylene

Powder of a silica-alumina catalyst (G) molded body was obtained from the silica-alumina catalyst (G) with use of the press machine and the sieves as in Example 1. Production of propylene was carried out in the same manner as in Example 1 except that the catalyst layer with a filling volume of 5.77 ml was formed after the silica-alumina catalyst (G) molded body had been dried at 200° C. for 2 hours and that the temperature of the vaporizer was set to 210° C., and analysis of a liquid component and a gas component was carried out in the same manner as in Example 1.

Comparative Example 3 a. Production Method for Silica-Alumina Catalyst (H)

4.57 g of the powder of the silica-alumina catalyst (A) molded body was placed in a muffle furnace and was calcined at 1000° C. for 1 hour to obtain 4.18 g of silica-alumina catalyst (H) molded body.

b. Production of Propylene 4.00 g of powder of the silica-alumina catalyst (H) molded body was filled into a SUS reaction tube that had an inner diameter of 1.4 cm and that included a SUS tube which had an outer diameter of 3 mm and which contained a thermocouple, so that a catalyst layer with a filling volume of 4.62 ml was formed. Thereafter, the temperature of the catalyst layer was increased in a reaction tube heating furnace over 45 minutes from room temperature to 200° C. under the flow of nitrogen at a rate of 110.0 N ml/min. A water-containing IPA raw material containing water 1 time as much by mass as IPA was introduced under the flow of nitrogen into a vaporizer heated to 210° C. at a flow rate of 0.237 ml/min with use of a feeding pump, and was then introduced into a reaction tube connected to a rear stage of the vaporizer. After that, the temperature of the reaction tube heating furnace was adjusted so that the temperature of the center of the catalyst layer was about 200° C. After a lapse of 30 minutes since the temperature of the catalyst layer had been adjusted, a liquid from the reaction tube was collected in two glass trap containers containing 25 g of methanol for 35 minutes, and a liquid component was analyzed by gas chromatography. After a lapse of 34 minutes following the collection of the liquid, a gas component exiting from the outlet of the two glass trap containers containing methanol was collected in a gas bag, and the gas component was analyzed by gas chromatography.

Example 6

Production of Propylene

After the powder of the silica-alumina catalyst (A) molded body was vacuum-dried at 200° C. for 2 hours, a catalyst layer with a filling volume of 5.77 ml was formed. Thereafter, the temperature of the catalyst layer was increased in a reaction tube heating furnace over 70 minutes from room temperature to 300° C. under the flow of nitrogen at a rate of 136.7 N ml/min. A water-containing NPA raw material containing water 1 time as much by mass as NPA was introduced under the flow of nitrogen into a vaporizer heated to 210° C. at a flow rate of 0.298 ml/min with use of a feeding pump, and was then introduced into a reaction tube connected to a rear stage of the vaporizer. After that, the temperature of the reaction tube heating furnace was adjusted so that the temperature of the center of the catalyst layer was about 300° C. After a lapse of 30 minutes since the temperature of the catalyst layer had been adjusted, a solution from the reaction tube was collected in two glass trap containers containing 26 g of methanol for 36 minutes, and a liquid component was analyzed by gas chromatography. After a lapse of 34 minutes following the collection of the liquid, a gas component exiting from the outlet of the two glass trap containers containing methanol was collected in a gas bag, and the gas component was analyzed by gas chromatography.

Comparative Example 4

Production of Propylene

Production of propylene was carried out in the same manner as in Example 6 except that the catalyst layer with a filling volume of 5.77 ml was formed after the silica-alumina catalyst (B) had been vacuum-dried at 200° C. for 2 hours, and analysis of a liquid component and a gas component was carried out in the same manner as in Example 6.

Example 7 a. Production Method for Silica-Alumina Catalyst (I)

Put into a 200-ml glass beaker were 59.88 g of pure water, 23.17 g of aluminum nitrate nonahydrate, and 13.07 g of citric acid, and a resulting mixture was stirred at room temperature for 5 minutes. While the stirring of the mixture in the beaker at room temperature was continued, 71.67 g of tetraethyl orthosilicate was dropped over 1 hour from a dropping burette to obtain a gel. The gel was transferred to a porcelain dish, dried in air at room temperature for 24 hours, and then dried in an evaporator under reduced pressure of 160 hPa at a water bath temperature of 50° C. to obtain 65.67 g of powder. In a muffle furnace, 30.40 g of the powder thus obtained was calcined at 800° C. for 2 hours to obtain 10.11 g of silica-alumina catalyst (I).

Production of Propylene

Powder of a silica-alumina catalyst (I) molded body was obtained from the silica-alumina catalyst (I) with use of the press machine and the sieves as in Example 1. Production of propylene was carried out in the same manner as in Example 6 except that the catalyst layer with a filling volume of 5.77 ml was formed after the silica-alumina catalyst (I) molded body had been dried at 200° C. for 2 hours, and analysis of a liquid component and a gas component was carried out in the same manner as in Example 6.

Comparative Example 5

Production of Propylene

Production of propylene was carried out in the same manner as in Example 6 except that the catalyst layer with a filling volume of 5.77 ml was formed after the silica-alumina catalyst (H) molded body had been dried at 200° C. for 2 hours, and analysis of a liquid component and a gas component was carried out in the same manner as in Example 6.

Example 8

Production of Propylene

The powder of the silica-alumina catalyst (A) molded body was filled into a SUS reaction tube to form a catalyst layer with a filling volume of 5.77 ml. Thereafter, the temperature of the catalyst layer was increased in a reaction tube heating furnace over 40 minutes from room temperature to 180° C. under the flow of nitrogen at a rate of 267.0 N ml/min. A water-containing IPA raw material containing water 0.2 times as much by mass as IPA was introduced under the flow of nitrogen into a vaporizer heated to 110° C. at a flow rate of 0.193 ml/min with use of a feeding pump, and was then introduced into a reaction tube connected to a rear stage of the vaporizer. After that, the temperature of the reaction tube heating furnace was adjusted so that the temperature of the center of the catalyst layer was about 180° C. After a lapse of 30 minutes since the temperature of the catalyst layer had been adjusted, a liquid from the reaction tube was collected in two glass trap containers containing 25 g of methanol for 34 minutes, and a liquid component was analyzed by gas chromatography. After a lapse of 33 minutes following the collection of the liquid, a gas component exiting from the outlet of the two glass trap containers containing methanol was collected in a gas bag, and the gas component was analyzed by gas chromatography.

Example 9

Production of Propylene

Production of propylene was carried out in the same manner as in Example 8 except that the flow rate of nitrogen was set to 270.0 N ml/min and that a water-containing IPA raw material containing water 0.2 times as much by mass as IPA and containing 2-methyl-1-pentene, which is olefin, 0.058 times as much by mass as IPA was used, and analysis of a liquid component and a gas component was carried out in the same manner as in Example 8.

Results

Table 1 shows $SiO_2/Al_2O_3$ ratios of the catalysts in Examples 1 to 5 and Comparative Examples 1 to 3, calcination temperatures thereof, and propylene yields calculated by gas chromatographic analyses on liquid components and gas components.

| | Example 1 | Comparative Example 1 | Example 2 | Example 3 | Comparative Example 2 | Example 4 | Example 5 | Comparative Example 3 |
|---|---|---|---|---|---|---|---|---|
| Catalyst | Silica-alumina catalyst (A) molded body | Silica-alumina catalyst (B) | Silica-alumina catalyst (C) molded body | Silica-alumina catalyst (D) molded body | Silica-alumina catalyst (E) | Silica-alumina catalyst (F) molded body | Silica-alumina catalyst (G) molded body | Silica-alumina catalyst (H) molded body |
| Catalyst calcination temperature (° C.) | 600 | 500 | 600 | 600 | 300 | 500 | 900 | 1000 |
| Raw materials for reaction (weight ratio) | IPA/water 50/50 | IPA/water 50/50 | IPA/water 50/50 | IPA/water 50/50 | Brown coloration and impossibility of molding | IPA/water 50/50 | IPA/water 50/50 | IPA/water 50/50 |
| Catalyst layer center temperature (° C.) | 200 | 200 | 200 | 200 | | 200 | 200 | 200 |
| $SiO_2/Al_2O_3$ (molar ratio) (ICP analysis value) | 11 | 404 | 51 | 69 | | 11 | 11 | 11 |
| Propylene yield (%) | 96.78 | 0 | 97.75 | 78.23 | | 74.46 | 92.59 | 0 |

Table 2 shows $SiO_2/Al_2O_3$ ratios of the catalysts in Examples 6 and 7 and Comparative Examples 4 and 5, calcination temperatures thereof, and propylene yields calculated by gas chromatographic analyses on liquid components and gas components.

TABLE 2

| | Example 6 | Comparative Example 4 | Example 7 | Comparative Example 5 |
|---|---|---|---|---|
| Catalyst | Silica-alumina catalyst (A) molded body | Silica-alumina catalyst (B) | Silica-alumina catalyst (I) molded body | Silica-alumina catalyst (H) molded body |
| Catalyst calcination temperature (° C.) | 600 | 500 | 800 | 1000 |
| Raw materials for reaction (weight ratio) | NPA/water 50/50 | NPA/water 50/50 | NPA/water 50/50 | NPA/water 50/50 |
| Catalyst layer center temperature (° C.) | 300 | 300 | 300 | 300 |
| $SiO_2/Al_2O_3$ (molar ratio) (ICP analysis value) | 11 | 404 | 11 | 11 |
| Propylene yield (%) | 91.98 | 0 | 93.75 | 15.36 |

Table 3 shows $SiO_2/Al_2O_3$ ratios of the silica-alumina catalyst (A) molded bodies in Examples 8 and 9, calcination temperatures thereof, and propylene yields calculated by gas chromatographic analyses on liquid components and gas components.

TABLE 3

| | Example 8 | Example 9 |
|---|---|---|
| Catalyst | Silica-alumina catalyst (A) molded body | Silica-alumina catalyst (A) molded body |
| Raw materials for reaction (weight ratio) | IPA/water 83.3/16.7 | IPA/water/2-methyl-1-pentene 79.5/15.9/4.6 |
| Catalyst layer center temperature (° C.) | 180 | 180 |
| $SiO_2/Al_2O_3$ (molar ratio) (ICP analysis value) | 11 | 11 |
| Propylene yield (%) | 81.35 | 53.66 |

From Table 1, it can be seen that, in a case where the silica-alumina catalyst (A) molded body in Example 1, the silica-alumina catalyst (C) molded body in Example 2, the silica-alumina catalyst (D) molded body in Example 3, the silica-alumina catalyst (F) molded body in Example 4, and the silica-alumina catalyst (G) molded body in Example 5 were used, IPA was mostly converted to propylene. On the other hand, in a case where the silica-alumina catalyst (B) with a high molar ratio of $SiO_2$ in Comparative Example 1 was used, the amount of propylene produced was below the detection limit value, and IPA was not converted to propylene at all. In addition, in a case where the silica-alumina catalyst (E) the calcination temperature of which was 300° C. in Comparative Example 2 was used, it was impossible to mold the catalyst. Furthermore, in a case where the silica-alumina catalyst (H) molded body the calcination temperature of which was 1000° C. in Comparative Example 3 was used, the amount of propylene produced was smaller than the amounts of propylene produced in Examples 1, 4, and 5. Thus, it has been shown that, with use of a silica-alumina catalyst in accordance with an embodiment of the present invention, it is possible to efficiently produce propylene from an IPA raw material containing much water.

From Table 2, it can be seen that, in a case where the silica-alumina catalyst (A) molded body in Example 6 and the silica-alumina catalyst (I) molded body in Example 7 were used, NPA was mostly converted to propylene. On the other hand, in a case where the silica-alumina catalyst (B) with a high molar ratio of $SiO_2$ in Comparative Example 4 was used, the amount of propylene produced was below the detection limit value, and NPA was not converted to propylene at all. Further, in a case where the silica-alumina catalyst (H) molded body the calcination temperature of which was 1000° C. in Comparative Example 5 was used, the amount of propylene produced was smaller than the amounts of propylene produced in Examples 6 and 7. Thus, it has been shown that, with use of a silica-alumina catalyst in accordance with an embodiment of the present invention, it is possible to efficiently produce propylene from an NPA raw material containing much water.

Table 3 shows that, in a case where the water-containing IPA raw material containing water 0.2 times as much by mass as IPA in Example 8, the propylene yield was 81.35%. On the other hand, in a case where the water-containing IPA raw material containing water 0.2 times as much by mass as IPA in Example 9 and containing 2-methyl-1-pentene 0.058 times as much by mass as IPA in Example 9 was used, the propylene yield was 53.66%. Note that the amount of 2-methyl-1-pentene contained in propylene obtained in Example 9 was 0.04 in terms of a molar ratio. Thus, it has been shown that the propylene yield is enhanced in a case where the raw material does not contain 2-methyl-1-pentene.

INDUSTRIAL APPLICABILITY

The present invention can be suitably utilized as a method for producing propylene.

The invention claimed is:

1. A method for producing propylene, the method comprising a dehydration reaction step of dehydrating a raw material containing propanol and water with use of a catalyst containing silica-alumina, the silica-alumina having a $SiO_2$ content of 3 to 80 in terms of a molar ratio with respect to $Al_2O_3$, wherein the catalyst containing the silica-alumina is produced by a sol-gel or impregnation production method including a step of carrying out calcination at a calcination temperature of not lower than 400° C. and not higher than 950° C.

2. The method according to claim 1, wherein a mass of the water in the raw material is 0.01 times to 2 times the mass of the propanol in the raw material.

3. The method according to claim 1, wherein a catalyst layer containing the catalyst has a temperature of not higher than 450° C. in the dehydration reaction step.

4. The method according to claim 1, wherein a fluid produced in the dehydration reaction step contains at least one of olefins represented by the following general formula (1) or (2) in an amount of not more than 0.1 in terms of a molar ratio with respect to the amount of propylene in the fluid, (1)

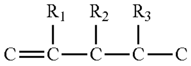

(2)

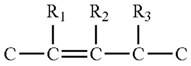

where, in the general formulas (1) and (2), any one of $R_1$, $R_2$, and $R_3$ is a methyl group, and the others are hydrogen.

5. The method according to claim 2, wherein a catalyst layer containing the catalyst has a temperature of not higher than 450° C. in the dehydration reaction step.

6. The method according to claim 2, wherein a fluid produced in the dehydration reaction step contains at least one of olefins represented by the following general formula (1) or (2) in an amount of not more than 0.1 in terms of a molar ratio with respect to the amount of propylene in the fluid, (1)

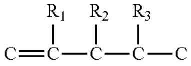

(2)

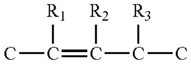

where, in the general formulas (1) and (2), any one of $R_1$, $R_2$, and $R_3$ is a methyl group, and the others are hydrogen.

* * * * *